(12) United States Patent
Nakamura et al.

(10) Patent No.: US 11,446,113 B2
(45) Date of Patent: Sep. 20, 2022

(54) SURGERY SUPPORT SYSTEM, DISPLAY CONTROL DEVICE, AND DISPLAY CONTROL METHOD

(71) Applicant: SONY CORPORATION, Tokyo (JP)

(72) Inventors: Takuya Nakamura, Tokyo (JP); Shinji Katsuki, Tokyo (JP); Mitsuaki Shiraga, Tokyo (JP); Manabu Hatakenaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/250,753

(22) PCT Filed: Sep. 6, 2019

(86) PCT No.: PCT/JP2019/035134
§ 371 (c)(1),
(2) Date: Mar. 1, 2021

(87) PCT Pub. No.: WO2020/054595
PCT Pub. Date: Mar. 19, 2020

(65) Prior Publication Data
US 2021/0346116 A1    Nov. 11, 2021

(30) Foreign Application Priority Data
Sep. 11, 2018   (JP) .............................. JP2018-169811

(51) Int. Cl.
*A61B 90/00*    (2016.01)
*H04N 13/167*   (2018.01)
(Continued)

(52) U.S. Cl.
CPC .......... *A61B 90/37* (2016.02); *A61B 1/00045* (2013.01); *A61B 90/20* (2016.02);
(Continued)

(58) Field of Classification Search
CPC ..... A61B 90/37; A61B 1/00045; A61B 90/20; A61B 2090/502; A61B 1/00006;
(Continued)

(56) References Cited

U.S. PATENT DOCUMENTS 6,575,969 B1 * 6/2003 Rittman, III ....... A61B 18/1482
606/41
6,636,254 B1   10/2003 Onishi et al.
(Continued)

FOREIGN PATENT DOCUMENTS

CN    1317197 A    10/2001
EP    0655710 A2   5/1995
(Continued)

OTHER PUBLICATIONS

International Search Report and Written Opinion of PCT Application No. PCT/JP2019/035134, dated Dec. 33, 2019, 14 pages of ISRWO.

*Primary Examiner* — Tung T Vo
(74) *Attorney, Agent, or Firm* — Chip Law Group

(57) ABSTRACT

The present disclosure relates to a surgery support system, a display control device, and a display control method in which a plurality of images can be displayed in an easy-to-see and efficient manner. An information processing device generates a composite image by compositing images output from a plurality of electronic instruments including a medical instrument, and adds, to the composite image, metadata related to division of the composite image. The display control device controls a display device to display, in the virtual three-dimensional space, divided images obtained by dividing the composite image into a plurality of divided regions on the basis of the metadata. The present disclosure can be applied to an endoscopic surgical system, for example.

19 Claims, 14 Drawing Sheets

(51) Int. Cl.
    *H04N 13/361* (2018.01)
    *H04N 5/262* (2006.01)
    *A61B 90/20* (2016.01)
    *H04N 13/332* (2018.01)
    *H04N 13/383* (2018.01)
    *H04N 13/156* (2018.01)
    *H04N 13/178* (2018.01)
    *A61B 1/00* (2006.01)
    *A61B 90/50* (2016.01)

(52) U.S. Cl.
    CPC ......... *H04N 5/2624* (2013.01); *H04N 5/2628* (2013.01); *H04N 13/156* (2018.05); *H04N 13/167* (2018.05); *H04N 13/178* (2018.05); *H04N 13/332* (2018.05); *H04N 13/361* (2018.05); *H04N 13/383* (2018.05); *A61B 2090/502* (2016.02)

(58) Field of Classification Search
    CPC ...... A61B 1/00039; A61B 2017/00203; A61B 2017/00207; A61B 90/361; A61B 2017/00216; A61B 2090/372; A61B 1/045; H04N 5/2624; H04N 5/2628; H04N 13/156; H04N 13/167; H04N 13/178; H04N 13/332; H04N 13/361; H04N 13/383; H04N 13/293; H04N 13/344; H04N 7/18; G02B 21/36; G02B 23/24; G06T 19/00
    USPC .......................................... 348/43
    See application file for complete search history.

(56) References Cited

U.S. PATENT DOCUMENTS

| | | | |
|---|---|---|---|
| 10,918,445 B2 * | 2/2021 | Swayze | A61B 90/37 |
| 2008/0183040 A1 | 7/2008 | Abe | |
| 2009/0036902 A1 * | 2/2009 | DiMaio | A61B 34/30 |
| | | | 606/130 |
| 2010/0305928 A1 * | 12/2010 | Cohen | G16H 50/50 |
| | | | 703/11 |
| 2010/0331855 A1 * | 12/2010 | Zhao | A61B 34/30 |
| | | | 606/130 |
| 2013/0047103 A1 * | 2/2013 | Avisar | G16H 50/50 |
| | | | 715/764 |
| 2017/0367771 A1 * | 12/2017 | Tako | A61B 34/20 |
| 2018/0168733 A1 * | 6/2018 | Swayze | A61B 34/30 |
| 2018/0296077 A1 | 10/2018 | Suzuki et al. | |
| 2018/0329609 A1 * | 11/2018 | De Swarte | G06T 19/00 |
| 2018/0357514 A1 * | 12/2018 | Zisimopoulos | G06N 3/0472 |
| 2019/0110856 A1 * | 4/2019 | Barral | G16H 30/40 |
| 2019/0286652 A1 * | 9/2019 | Habbecke | G16H 30/20 |
| 2021/0015432 A1 * | 1/2021 | Konno | A61B 90/361 |
| 2021/0065746 A1 * | 3/2021 | Sugano | H04N 5/23216 |
| 2021/0203875 A1 * | 7/2021 | Sakurada | A61B 1/045 |
| 2021/0249109 A1 * | 8/2021 | Hayashi | G06F 21/6245 |

FOREIGN PATENT DOCUMENTS

| | | |
|---|---|---|
| EP | 1929933 A2 | 6/2008 |
| JP | 07-265264 A | 10/1995 |
| JP | 2001-022335 A | 1/2001 |
| JP | 2001-117046 A | 4/2001 |
| JP | 2006-122375 A | 5/2006 |
| JP | 2007-081863 A | 3/2007 |
| JP | 2008-036318 A | 2/2008 |
| JP | 2009-239762 A | 10/2009 |
| JP | 2015-019679 A | 2/2015 |
| JP | 2018-061181 A | 4/2018 |
| WO | 01/05144 A1 | 1/2001 |
| WO | 2017/104197 A1 | 6/2017 |
| WO | 2017/168622 A1 | 10/2017 |
| WO | 2018/147329 A1 | 8/2018 |

* cited by examiner

SURGERY SUPPORT SYSTEM, DISPLAY CONTROL DEVICE, AND DISPLAY CONTROL METHOD

CROSS REFERENCE TO RELATED APPLICATIONS

This application is a U.S. National Phase of International Patent Application No. PCT/JP2019/035134 filed on Sep. 6, 2019, which claims priority benefit of Japanese Patent Application No. JP 2018-169811 filed in the Japan Patent Office on Sep. 11, 2018. Each of the above-referenced applications is hereby incorporated herein by reference in its entirety.

TECHNICAL FIELD

The present disclosure relates to a surgery support system, a display control device, and a display control method, and particularly to a surgery support system, a display control device, and a display control method in which a plurality of images can be displayed in an easy-to-see and efficient manner.

BACKGROUND ART

In recent years, there have been an increasing number of surgical operations in which an operative field image captured by an endoscope or a video microscope is displayed on a monitor and an operator performs the surgical operation while looking at the monitor. It has been proposed to increase the efficiency of surgical operations by displaying an image obtained by MRI inspection or X-ray inspection on another monitor at the same time to make it easy to check the conditions of the patient.

In this case, a plurality of monitors is needed for displaying images from a plurality of instrument, and the region occupied by the monitors in the operating room is increased.

In contrast, for example, Patent Document 1 proposes integrating images from a plurality of instruments and displaying them on one screen. Furthermore, Patent Document 2 proposes two-dimensionally displaying images from a plurality of instruments on an HMD.

CITATION LIST

Patent Document

Patent Document 1: Japanese Patent Application Laid-Open No. 2006-122375
Patent Document 2: Japanese Patent Application Laid-Open No. 2015-019679

SUMMARY OF THE INVENTION

Problems to be Solved by the Invention

However, a monitor having a large display region is needed in order to display a plurality of images on one screen. Furthermore, there are limited angles at which images displayed on the monitor can be viewed, and a plurality of monitors is needed in order for all the member in the operating room to see the images. As a result, the region occupied by the monitors in the operating room is increased.

Furthermore, in the case of two-dimensionally displaying a plurality of images on an HMD, the plurality of images is displayed in a limited display region, and thus there has been a tendency that each image has a small display size.

The present disclosure has been made in view of such circumstances and is to make it possible to display a plurality of images in an easy-to-see and efficient manner.

Solutions to Problems

A surgery support system of the present disclosure is a surgery support system including: an information processing device including: a composition section that generates a composite image by compositing images output from a plurality of electronic instruments including a medical instrument; and a metadata addition section that adds, to the composite image, first metadata related to division of the composite image; and a display control device including: a display control section that controls a display device to display, in a virtual three-dimensional space, divided images obtained by dividing the composite image into a plurality of divided regions on the basis of the first metadata.

A display control device of the present disclosure is a display control device including: a display control section that controls a display device to display, in a virtual three-dimensional space, divided images obtained by dividing a composite image into a plurality of divided regions on the basis of metadata related to division of the composite image, the composite image generated by compositing images output from a plurality of electronic instruments including a medical instrument.

A display control method of the present disclosure is a display control method including: controlling, by a display control device, a display device to display, in a virtual three-dimensional space, divided images obtained by dividing a composite image into a plurality of divided regions on the basis of metadata related to division of the composite image, the composite image generated by compositing images output from a plurality of electronic instruments including a medical instrument.

In the present disclosure, a composite image is generated by compositing images output from a plurality of electronic instruments including a medical instrument, metadata related to division of the composite image is added to the composite image, and a display device is controlled to display, in a virtual three-dimensional space, divided images obtained by dividing the composite image into a plurality of divided regions on the basis of the metadata.

Effects of the Invention

According to the present disclosure, it is possible to display a plurality of images in an easy-to-see and efficient manner.

Modes for carrying out the present disclosure (hereinafter referred to as embodiments) will be described below. Note that the description will be given in the following order.

1. System configuration
2. Flow of image display process
3. Use of line-of-sight detection result
4. About 3D display
5. Application example
6. Hardware configuration <1. System configuration>

(Configuration of surgery support system)

Figure 1:
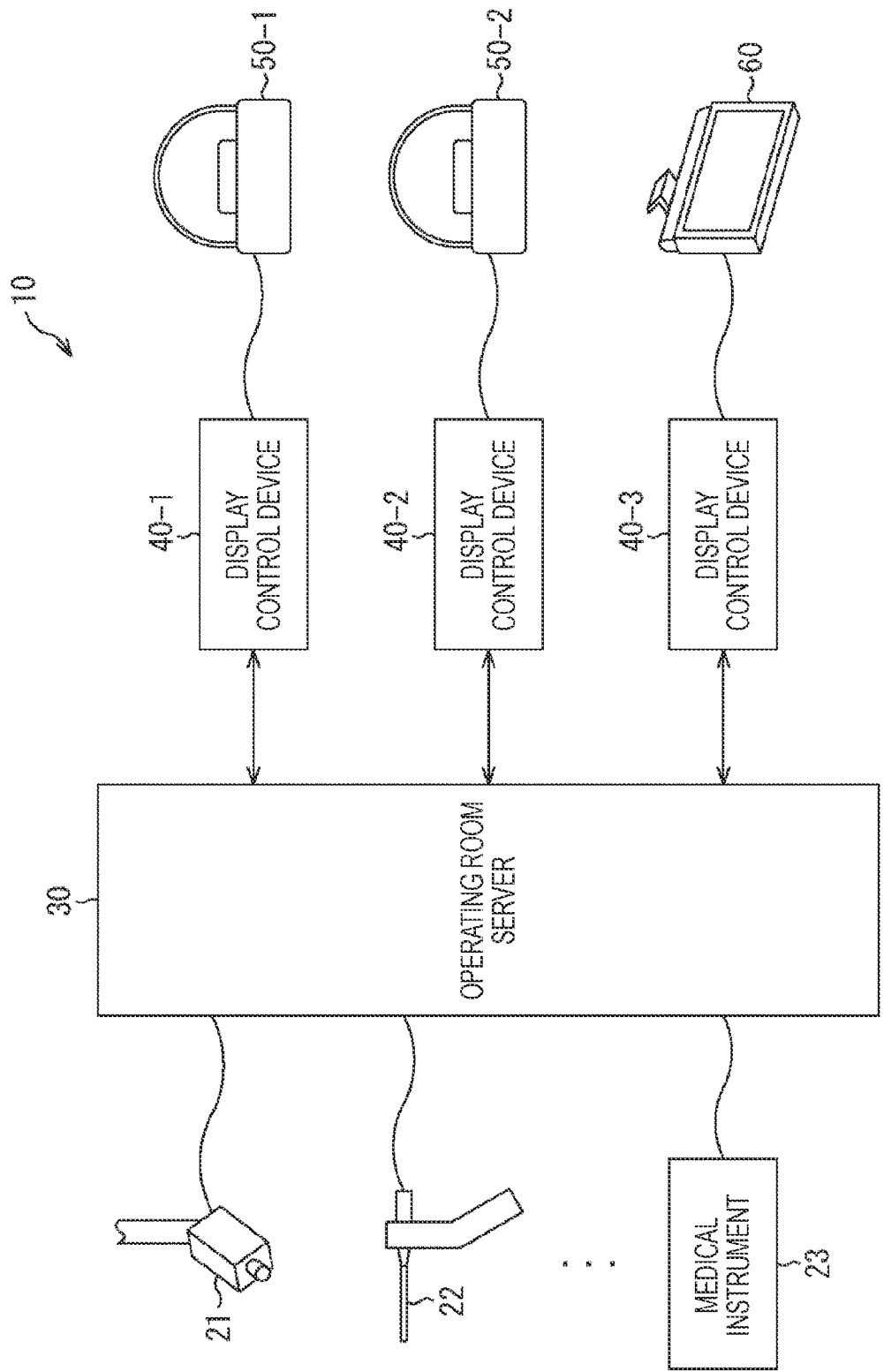
FIG. 1 is a diagram showing an example configuration of a surgery support system according to the present embodiment.

FIG. 1 is a diagram showing an example configuration of a surgery support system according to the present embodiment.

FIG. 1 shows an example of an endoscopic surgical system used in an endoscopic abdominal surgical operation, which is performed instead of conventional laparotomy in a medical setting, for example.

The surgery support system 10 includes an operating room camera 21, an endoscope device 22, a medical instrument 23, an operating room server 30, display control devices 40-1 to 40-3, HMDs 50-1 and 50-2, and a monitor 60.

The operating room camera 21 is provided on the ceiling of an operating room, for example, and captures an image of the entire space of the operating room and an image of the operator's hand.

The endoscope device 22 is constituted as an observation medical instrument for observing the inside of a body cavity of the patient, and a tubular insertion portion is inserted into the body cavity of the patient. The insertion portion of the endoscope device 22 is internally provided with an image sensor such as a complementary metal oxide semiconductor (CMOS) image sensor for capturing an image of the inside of the body cavity and an optical system such as a lens.

The numbers of image sensors, optical systems, and the like arranged in the endoscope device 22 are two in order to capture right-eye and left-eye images having parallax, for example. Therefore, a three-dimensional image that can three-dimensionally display the inside of the body cavity is acquired.

The medical instrument 23 is an electronic instrument that outputs an image and information related to medical treatment such as a surgical operation. The medical instrument 23 outputs an image used for diagnostic imaging, for example, an image and information obtained by magnetic resonance imaging (MRI) inspection, computed tomography (CT) inspection, ultrasonic inspection, X-ray inspection, or the like. The number of medical instruments 23 is not limited to one, and a plurality of medical instruments 23 may be provided.

Images output from the respective electronic instruments of the operating room camera 21, the endoscope device 22, and the medical instrument 23 are supplied to the operating room server 30. In particular, images output from the operating room camera 21 and the endoscope device 22 are real-time moving images.

The operating room server 30 generates a composite image by compositing images output from the respective electronic instruments. The composite image generated by the operating room server 30 is supplied to each of the display control devices 40-1 to 40-3.

The display control devices 40-1 to 40-3 causes divided images, which are obtained by dividing the composite image from the operating room server 30 into a plurality of divided regions, to be displayed on each of the head mounted displays (HMDs) 50-1 and 50-2 and the monitor 60 as display devices.

The HMDs 50-1 and 50-2 are mounted on the user's head. The user is a medical worker involved in a surgical operation performed in the operating room, for example, and includes an operating surgeon, an assistant, a scopist, and a nurse in the surgical operation, as well as a doctor monitoring the surgical operation from a location separate from the operating room, and the like.

The monitor 60 is constituted as a ceiling-hung monitor hung from the ceiling of the operating room, for example.

The HMDs 50-1 and 50-2 and the monitor 60 can realize the display of a virtual three-dimensional space (VR space).

Note that, in the following, the display control devices 40-1 to 40-3 are simply referred to as display control devices 40 in a case where they are not distinguished from each other. Furthermore, the HMDs 50-1 and 50-2 are simply referred to as HMDs 50 in a case where they are not distinguished from each other.

Furthermore, although the surgery support system 10 includes two HMDs 50 and one monitor 60 in FIG. 1, the number of HMDs 50 and the number of monitors 60 are not limited thereto.

(Configuration of HMD)

Figure 2:
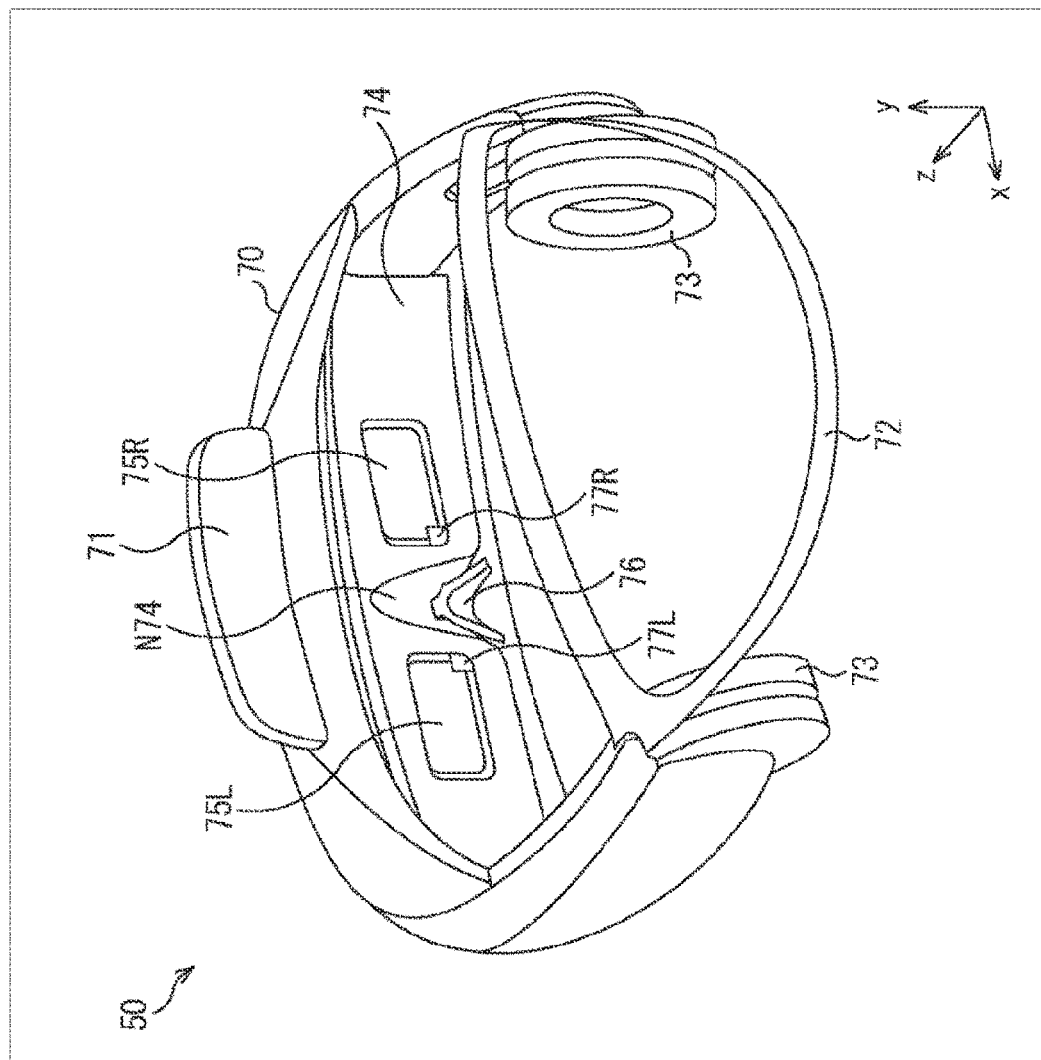
FIG. 2 is a perspective view showing an example configuration of an HMD.

FIG. 2 is a diagram showing an example configuration of an HMD 50. FIG. 2 is a perspective view of the HMD 50 as seen from the direction facing its display surface.

Note that the x-axis direction, y-axis direction, and z-axis direction indicate three axis directions that are orthogonal to each other in the xyz coordinate system to which the HMD 50 belongs. The x-axis direction is the left-right direction of the HMD 50. The y-axis direction is the up-down direction of the HMD 50. The z-axis direction is the front-rear direction of the HMD 50.

The HMD 50 is constituted by a housing 70 as a non-see-through HMD having a goggle shape as a whole, for example.

The housing 70 is arranged in front of the wearer's eyes and is configured to fit the wearer's face. The housing 70 is formed in a semicircular disc shape bulging in the z-axis direction as a whole, for example. A pad portion 71 that contacts the wearer's forehead at the time of mounting to fix the mounting position of the housing 70 is arranged on the upper surface of the housing 70. Furthermore, on the left and right side surfaces of the housing 70, a mounting portion 72 configured to allow the housing 70 to be mounted at an appropriate relative position is connected, and further, respective headphones 73 are arranged.

The housing 70 includes an eyepiece surface 74 that faces the wearer's face including the left and right eyes at a predetermined distance in the z-axis direction and is substantially orthogonal to the z-axis direction.

Display sections 75L and 75R are arranged side by side in the x-axis direction at positions on the eyepiece surface 74 corresponding to the wearer's left and right eyes. Note that it is desirable that optical lenses such as a magnifying lens for magnifying an image displayed on the display sections 75L and 75R and a correction lens for performing optical correction are provided near the display sections 75L and 75R.

The display sections 75L and 75R are configured to be able to present left-eye and right-eye images (left-eye image and right-eye image) acquired by the endoscope device 22 or the like to the left eye and right eye of the wearer, respectively. Here, in a case where the above-described optical lenses are provided, it is desirable that the left-eye image and the right-eye image have image distortion for neutralizing the distortion caused by the optical lenses.

A notch N74 is formed at the center of the eyepiece surface 74, for example, in conformity with the shape of the wearer's nose. A nose pad 76, for example, configured to be attachable and detachable is arranged at the notch N74.

Moreover, line-of-sight detection sensors 77L and 77R for detecting the line-of-sight of both of the left and right eyes of the wearer are provided on the notch N74 side of the respective display sections 75L and 75R on the eyepiece surface 74.

Furthermore, the HMD 50 includes a gyro sensor (not shown) capable of detecting acceleration along each of the x-axis direction, y-axis direction, and z-axis direction and angular velocity around the axis in each direction. The gyro sensor can detect the attitude of the HMD 50, that is, the movement of the wearer's head.

Note that the movement of the wearer's head (attitude of the HMD 50) may be detected on the basis of a result of image recognition on an image obtained by a camera that captures the outside of the HMD 50 (surroundings of the wearer). Furthermore, the movement of the wearer's head may be detected on the basis of a result of image recognition on an image obtained by capturing the external scenery by a camera attached to the HMD (such as change or movement of a subject in the image).

(Example functional configuration of surgery support system)

Figure 3:
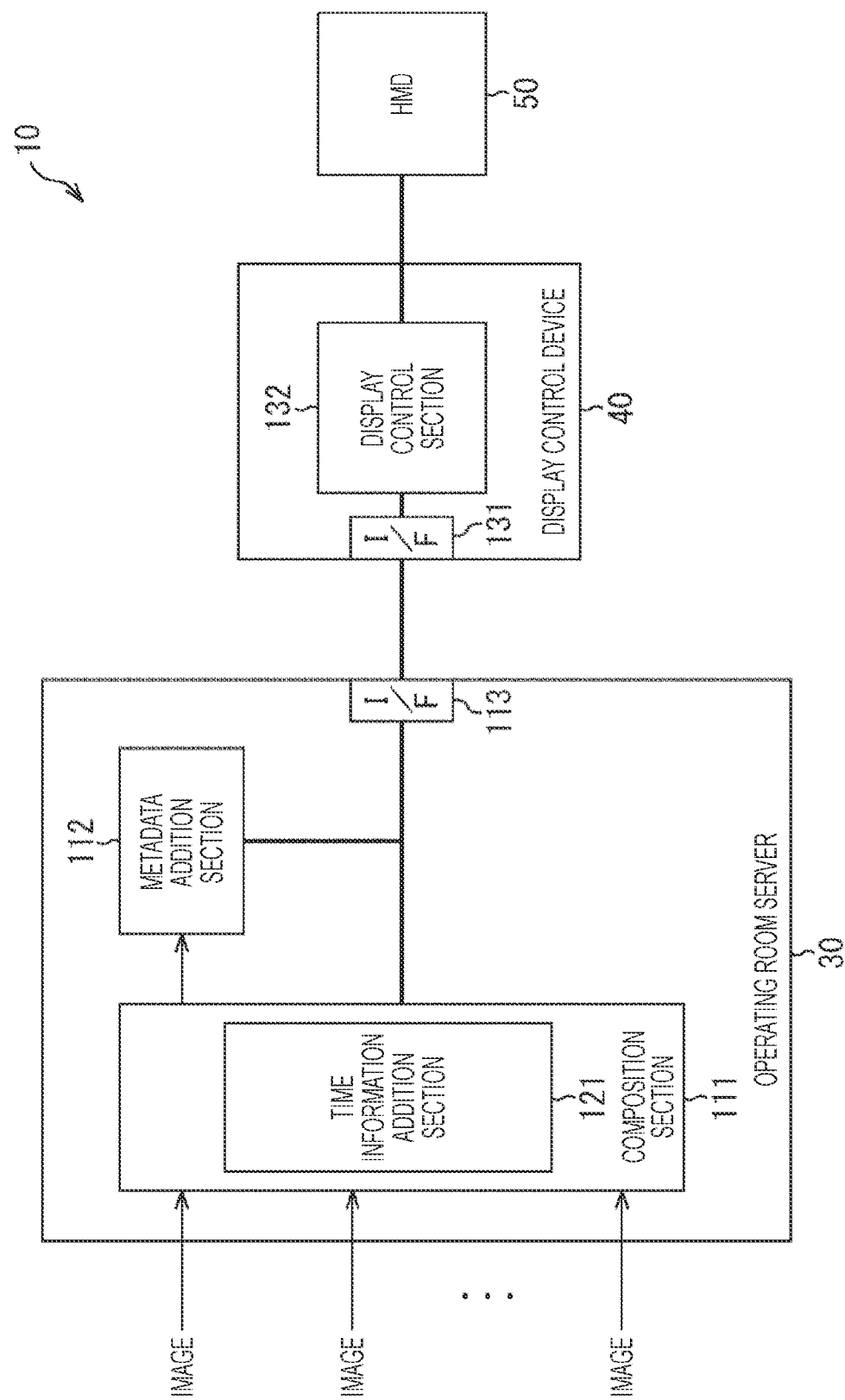
FIG. 3 is a block diagram showing an example functional configuration of a surgery support system.

FIG. 3 is a block diagram showing an example functional configuration of the surgery support system 10 described above.

The surgery support system 10 in FIG. 3 includes the operating room server 30 as an information processing device, a display control device 40, and the HMD 50 as a display device.

The operating room server 30 includes a composition section 111, a metadata addition section 112, and an I/F section 113.

The composition section 111 generates a composite image by compositing images output from the respective electronic instruments such as the operating room camera 21, the endoscope device 22, and the medical instrument 23, and supplies it to the I/F section 113.

The composition section 111 includes a time information addition section 121. The time information addition section 121 adds time information to each image when the composition section 111 composites the images output from the respective electronic instruments.

The metadata addition section 112 generates division metadata, which is first metadata related to division of the composite image, and display metadata, which is second metadata related to display of each divided image obtained by dividing the composite image into a plurality of divided regions, and adds them to the composite image.

The I/F section 113 sends/receives data to/from the display control device 40. The I/F section 113 complies with the Serial Digital Interface (SDI) standards, in which 4K resolution images can be transmitted, for example. The I/F section 113 transmits the composite image to which the division metadata and the display metadata are added to the display control device 40. The operating room server 30 (the I/F section 113) and the display control device 40 are connected by only one transmission path.

The display control device 40 includes an I/F section 131 and a display control section 132.

The I/F section 131 is connected to the I/F section 113 of the operating room server 30 by one transmission path, and sends/receives data to/from the operating room server 30. The I/F section 131 also complies with the SDI standards, in which 4K resolution images can be transmitted, for example. The I/F section 131 receives the composite image from the operating room server 30 and supplies it to the display control section 132.

The display control section 132 controls the display of the virtual three-dimensional space in the HMD 50.

Specifically, the display control section 132 controls the HMD 50 to display the divided images, which are obtained by dividing the composite image into a plurality of divided regions on the basis of the division metadata added to the composite image, in the virtual three-dimensional space.

Furthermore, the display control section 132 controls the display of the divided images in the virtual three-dimensional space on the basis of the display metadata added to the composite image.

Note that The display control section 132 performs image processing such as RAW development processing, noise removal processing, and color conversion processing on the divided images displayed in the virtual three-dimensional space, and further performs adjustment for appropriately displaying them in the virtual three-dimensional space.

<2. Flow of image display process>

Figure 4:
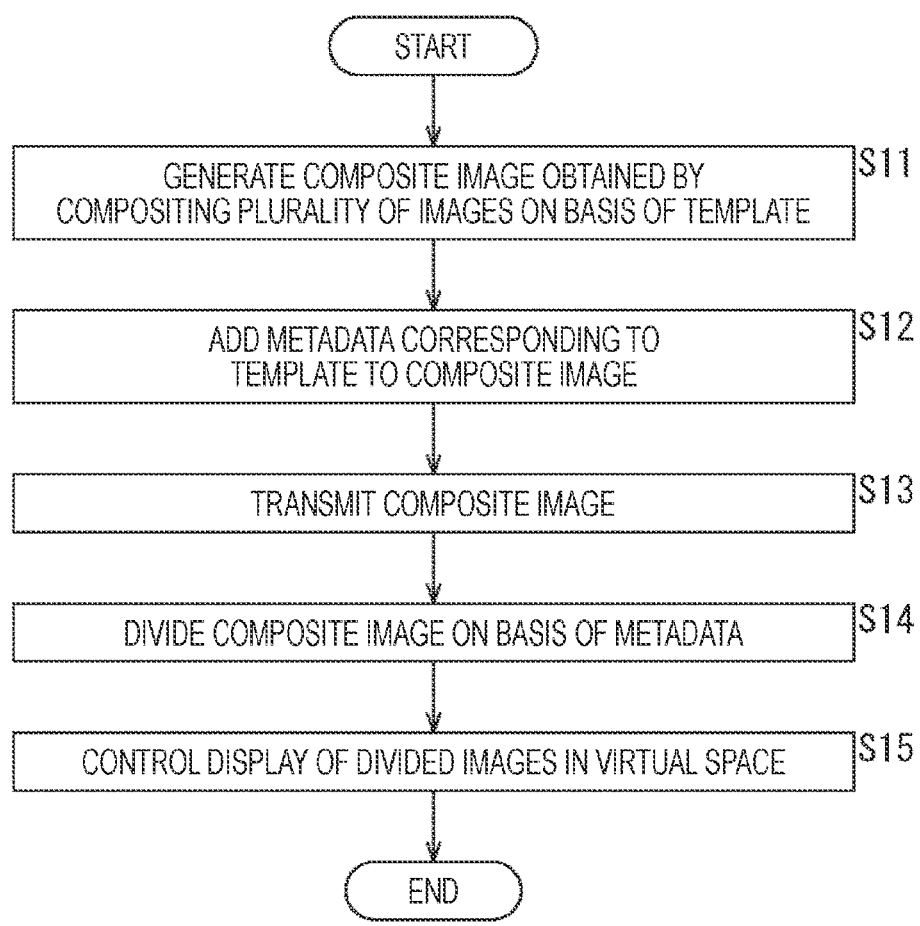
FIG. 4 is a flow chart illustrating an image display process.

Next, an image display process in the HMD 50 will be described with reference to the flow chart of FIG. 4.

In step S11, the composition section 111 of the operating room server 30 generates a composite image obtained by compositing a plurality of images on the basis of a template selected by a user wearing the HMD 50.

The template is data prepared for each type of the user such as an operating surgeon, an assistant, or a nurse, and includes information defining a combination of images needed for the user and information indicating the arrangement of the images when they are displayed on the HMD 50.

Figure 5:
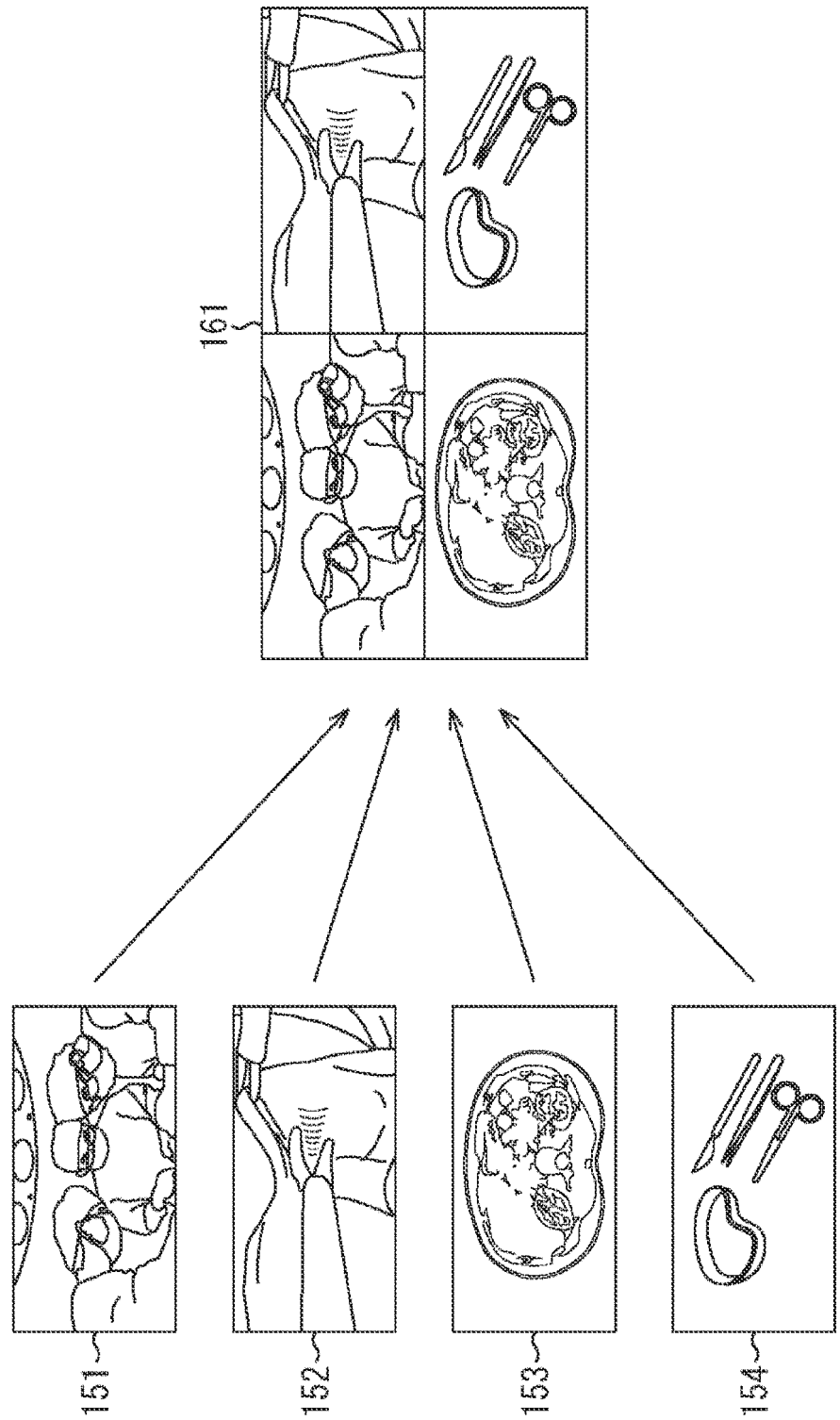
FIG. 5 is a diagram illustrating composition of images.

For example, in a case where an operating surgeon template is selected, as shown in FIG. 5, the composition section 111 generates a composite image 161 by compositing images 151 to 154 defined by the operating surgeon template out of the images output from the plurality of electronic instruments.

The image 151 is an image obtained by image capture of other users in the operating room, and the image 152 is an operative field image obtained by image capture of the inside of the body cavity of the patient by the endoscope device 22. The image 153 is a medical image obtained by MRI inspection, and the image 154 is an image obtained by image capture of surgical tools handled by a scrub nurse.

Each of the images 151 to 154 is an image having full high definition (HD) image quality, for example. In this case, the composite image 161 obtained by compositing the images 151 to 154 is a 4K resolution image.

Note that, when the composition section 111 generates the composite image 161, the time information addition section 121 adds time information to each of the images 151 to 154.

In step S12, the metadata addition section 112 generates division metadata and display metadata corresponding to the template selected by the user wearing the HMD 50 and adds them to the composite image.

The division metadata includes information indicating each of the divided regions for dividing the composite image by the display control device 40. For example, the information indicating the divided regions is information indicating the types of the medical instruments (electronic instruments) from which the images are output. That is, the divided regions are regions corresponding to the images output from the respective electronic instruments.

Furthermore, the display metadata includes arrangement information indicating the arrangement of each divided image in the virtual three-dimensional space and display size information indicating the display size of each divided image.

Therefore, the metadata addition section 112 generates division metadata and display metadata that realize a display manner of the divided images corresponding to the selected template, and adds them to the composite image. Note that division metadata and display metadata that are preset according to each template may be prepared in advance and added to the composite image.

In step S13, the I/F section 113 sends the composite image to which the division metadata and the display metadata are added to the display control device 40. The I/F section 131 of the display control device 40 receives the composite image from the operating room server 30 and supplies it to the display control section 132.

In step S14, the display control section 132 divides the composite image on the basis of the division metadata added to the composite image from the operating room server 30.

Figure 6:
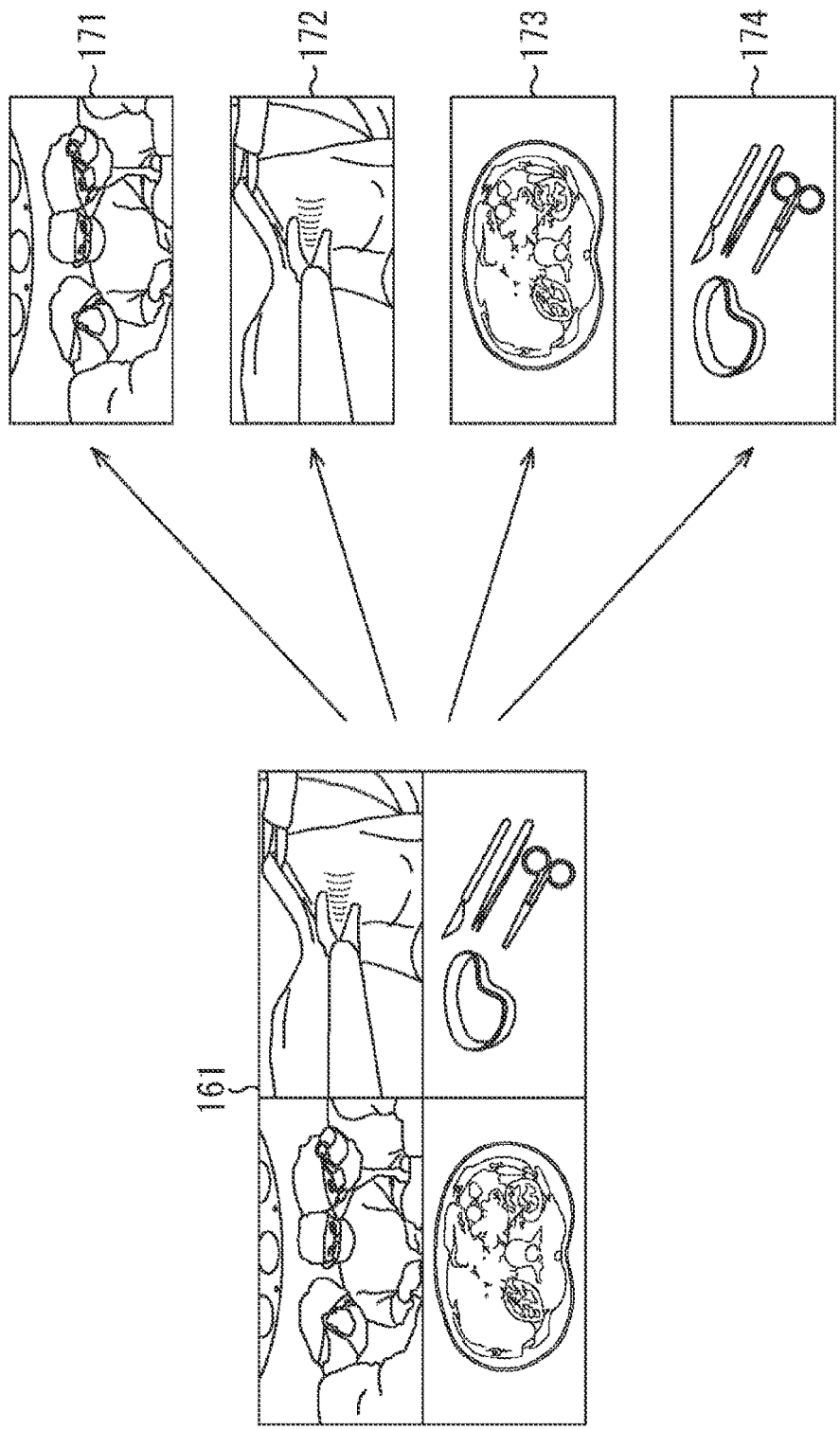
FIG. 6 is a diagram illustrating division of a composite image.

For example, as shown in FIG. 6, the display control section 132 generates divided images 171 to 174 by dividing the composite image 161 from the operating room server 30 on the basis of the information indicating the divided regions included in the division metadata. In this example, since the divided regions are regions corresponding to the images output from the respective electronic instruments, the divided images 171 to 174 are the same as the images 151 to 154, respectively.

In step S15, the display control section 132 controls the display of each divided image in the virtual three-dimensional space of the HMD 50 on the basis of the display metadata added to the composite image from the operating room server 30.

Since the display metadata includes the arrangement information and the display size information, each divided image is displayed in the arrangement indicated by the arrangement information and in the display size indicated by the display size information in the virtual three-dimensional space of the HMD 50.

Figure 7:
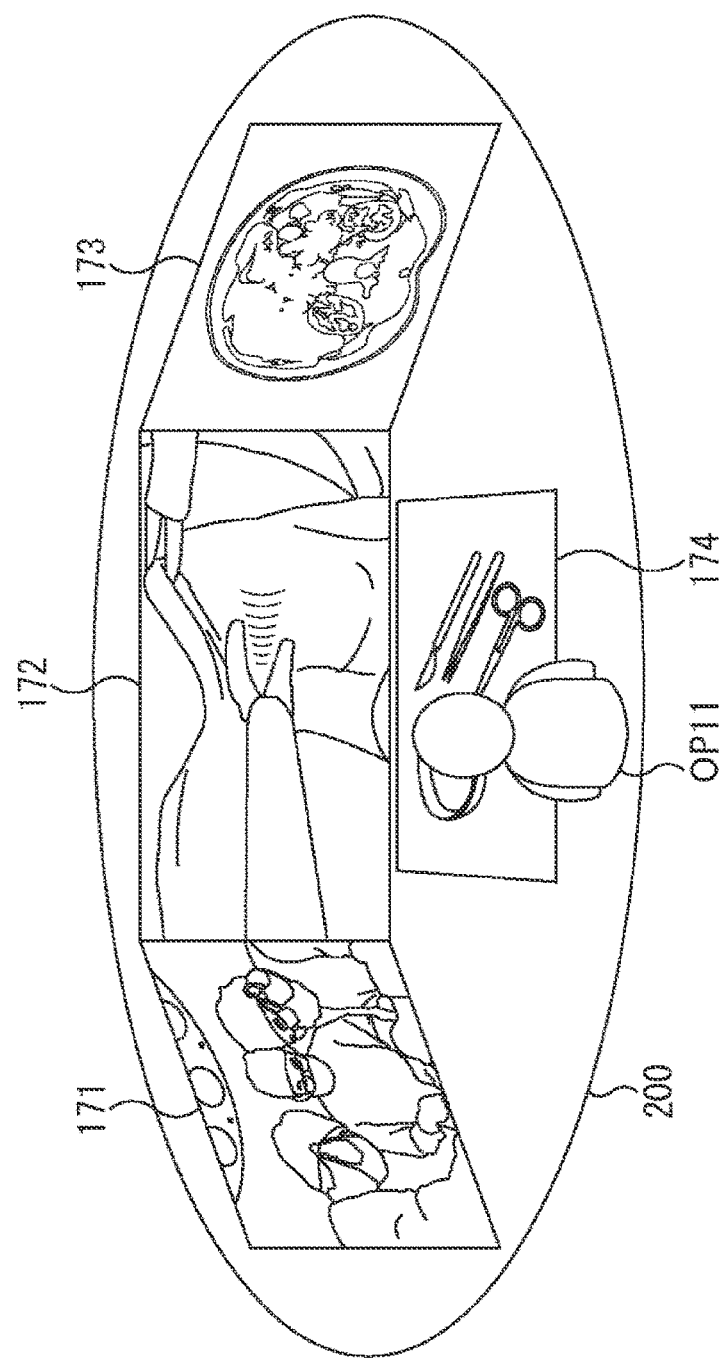
FIG. 7 is a diagram illustrating display in a virtual three-dimensional space.

FIG. 7 is a diagram illustrating display in the virtual three-dimensional space.

FIG. 7 shows how the divided images 171 to 174 are displayed in a three-dimensional arrangement in a virtual three-dimensional space 200. Note that a user OP11 in FIG. 7 is for indicating the point of view of an operating surgeon in the virtual three-dimensional space 200 and is not actually displayed.

The arrangement and the display sizes of the divided images 171 to 174 in the virtual three-dimensional space 200 are determined by the display metadata generated according to the operating surgeon template.

In the example of FIG. 7, since the user is an operating surgeon and the operating surgeon template is selected, the divided image 172, which is an operative field image obtained by image capture of the inside of the body cavity of the patient by the endoscope device 22, is arranged at the front of the field of view of the user OP11 and is displayed in a larger size than the other images. That is, in the example of FIG. 7, the divided image 172 is displayed as the main in the virtual three-dimensional space 200.

Furthermore, the divided image 171, which is obtained by image capture of other users in the operating room, is arranged at the left front of the field of view of the user OP11, and the divided image 173, which is obtained by MRI inspection, is arranged at the right front of the field of view of the user OP11. Moreover, the divided image 174, which is obtained by image capture of surgical tools, is arranged at a lower position in the field of view of the user OP11 and is displayed in a smaller size than the other images.

The display in the virtual three-dimensional space 200 changes in association with the movement of the head of the user wearing the HMD 50. Specifically, the position and size of each image in the virtual three-dimensional space 200 changes according to the movement of the user's head. For example, in the example of FIG. 7, in a case where the user's head rotates rightward to move the point of view in the right direction, the divided image 173 is arranged at the front of the field of view of the user OP11. Furthermore, in the example of FIG. 7, in a case where the user's head moves forward, the divided image 172 arranged at the front of the field of view of the user OP11 is displayed in a larger size.

Furthermore, in the virtual three-dimensional space 200, the divided images are displayed in synchronization with each other on the basis of time information added to the images from the respective medical instruments from which the divided images are generated.

With the above process, a plurality of images can be displayed in an easy-to-see and efficient manner in the virtual three-dimensional space without preparing a monitor with a large display region or a plurality of monitors or without reducing the display size of each image.

In particular, since there is no need to prepare a monitor with a large display region or a plurality of monitors, the cost and human effort required for purchasing, installing, and moving the monitor can be reduced while reducing the region occupied by the monitor in the operating room.

Although the user needs to grasp the surrounding conditions in the operating room such as actions of other users, vital signs of the patient, and the anesthetic condition besides the surgical portion, it has been difficult to grasp these surrounding conditions in a case of using an HMD.

Thus, in the present embodiment, images obtained by image capture of the inside of the operating room such as the image obtained by image capture of other users in the operating room, besides the operative field image, are displayed in the virtual three-dimensional space. Therefore, even in a case where the user uses an HMD, the surrounding conditions in the operating room can be grasped, and it is possible to prevent collision with other users, equipment, and the like in the operating room and to deal with changes in conditions in the operating room.

Figure 8:
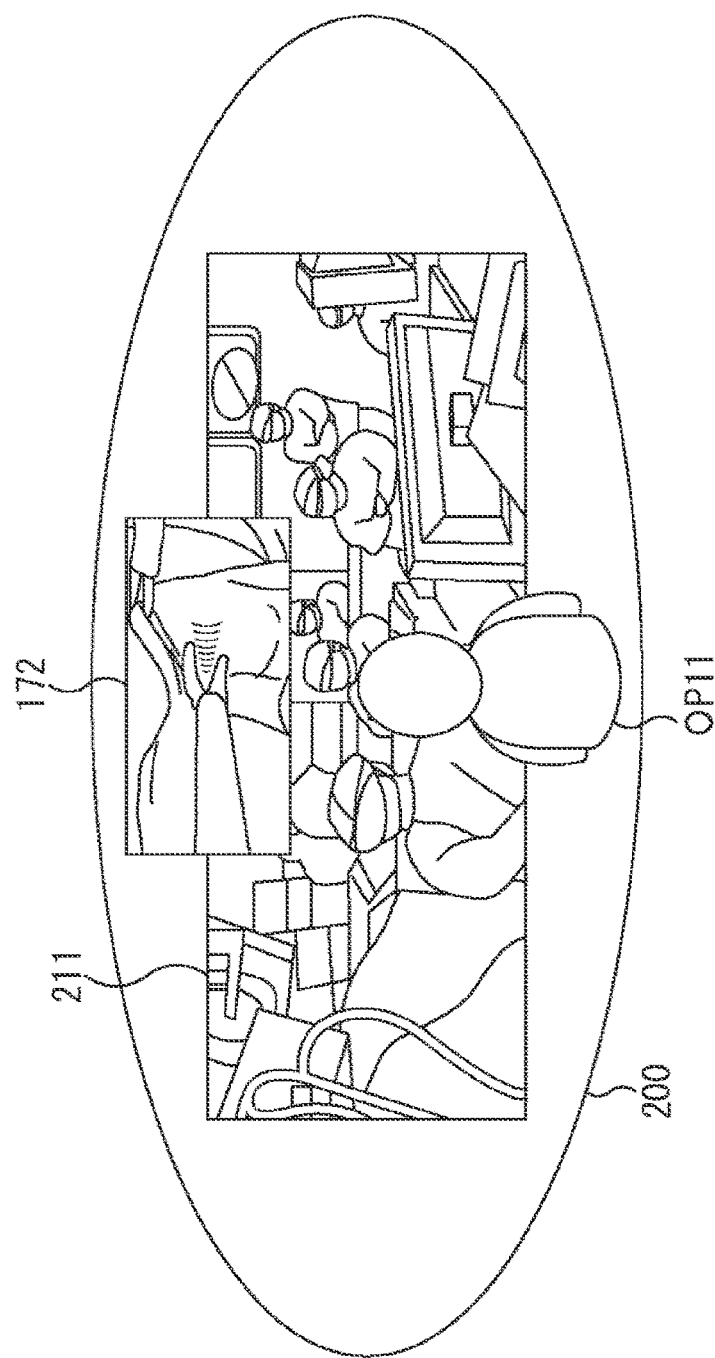
FIG. 8 is a diagram illustrating display in a virtual three-dimensional space.

In particular as shown in FIG. 8, a panoramic image 211 obtained by image capture of the inside of the operating room over a wide range may be arranged and displayed in the virtual three-dimensional space 200 as a divided image, in addition to the divided image 172, which is an operative field image. In this case, for example, the operating room camera 21 is constituted as a panoramic camera.

Therefore, the user can grasp the surrounding conditions in the operating room over a wider range than with the naked eye.

Furthermore, in a case where images from a plurality of medical instruments are displayed on the HMD at the same time, the same number of transmission paths as the number of medical instruments are needed, and the transmission cost is increased. In consideration of higher transmission speed, the cost is further increased.

Thus, in the present embodiment, the operating room server 30 transmits the composite image, which is obtained by compositing images from a plurality of medical instruments, to the display control device 40 in only one transmission path to display the divided images on the HMD. That is, the images from the plurality of medical instruments can be collectively transmitted as the composite image, and therefore the transmission cost can be reduced.

Incidentally, in a broadcasting station, a synchronization signal is input to a plurality of broadcasting instruments, so that the instruments can be synchronized with each other. On the other hand, in a medical institution, many medical instruments are used for a long period of time, and there has been instruments that do not support the input of the synchronization signal.

Thus, in the present embodiment, time information is added to the images from the respective medical instruments from which the divided images are generated. Therefore, the images can be displayed in the virtual three-dimensional space in synchronization with each other. Furthermore, by using the image displayed as the main in the virtual three-dimensional space as a master for the synchronization, the image displayed as the main can be displayed without causing a delay for synchronization adjustment.

Although an example where the operating surgeon template is selected has been described above, in a case where a template for another user type is selected, the images displayed in the virtual three-dimensional space 200 and their arrangement and display sizes will differ.

Figure 9:
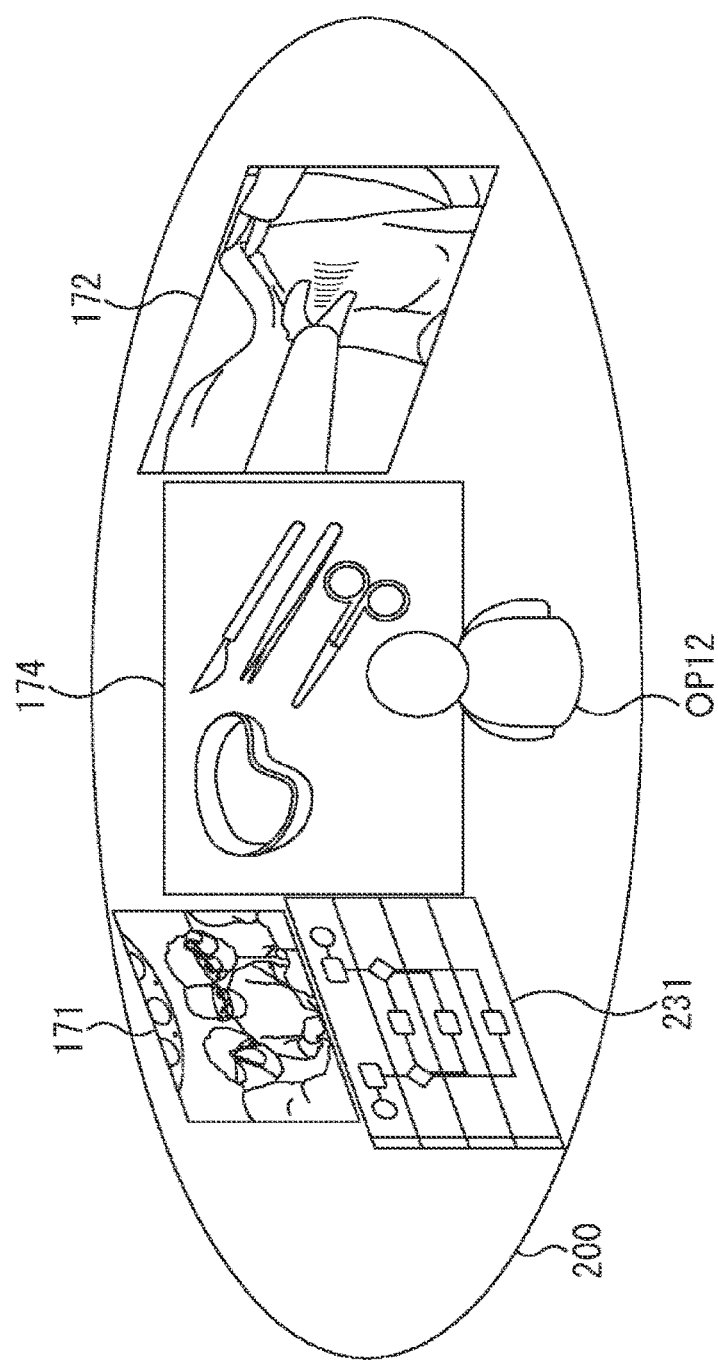
FIG. 9 is a diagram illustrating display in a virtual three-dimensional space.

For example, in a case where the user is a scrub nurse and a template for the nurse is selected, as shown in FIG. 9, the divided image 174, which is obtained by image capture of surgical tools, is arranged at the front of the field of view of the user OP12 and is displayed in a larger size than the other images. That is, in the example of FIG. 9, the divided image 174 is displayed as the main in the virtual three-dimensional space 200.

Furthermore, the divided image 171, which is obtained by image capture of other users in the operating room, is arranged at the upper left front of the field of view of the user OP12, and an image 231 indicating a surgical operation flow is arranged at a lower position of the divided image 171. The image 231 is an image that is not displayed in a case where the user is an operating surgeon. The divided image 172, which is an operative field image obtained by image capture of the inside of the body cavity of the patient by the endoscope device 22, is arranged at the right front of the field of view of the user OP12.

Note that a user OP12 in FIG. 9 is for indicating the point of view of the scrub nurse in the virtual three-dimensional space 200 and is not actually displayed.

In this manner, the images displayed in the virtual three-dimensional space 200 and their arrangement and display sizes are determined according to the template selected by the user. Therefore, each user can check images related to other users' tasks while gazing an image related to his/her own task (an image that the user himself/herself wants to see) in particular.

Furthermore, template settings (the images displayed in the virtual three-dimensional space 200 and their arrangement and display sizes) may be changed according to an instruction from the user. Therefore, the user can change the template settings according to the details of the surgical operation, for example.

Moreover, the template may be switched according to the progress of the surgical operation flow, and the template may be switched on the basis of a voice instruction of the user.

Note that the contents of the division metadata and the display metadata are changed in association with such change in settings or switching of the template.

Furthermore, the arrangement and display sizes of the images displayed in the virtual three-dimensional space 200 may be changed during the surgical operation. In this case, a change in the content of the display metadata that determines the arrangement and display sizes of the images is triggered by an operation by the user wearing the HMD 50 on a foot switch or an operation panel in the operating room, a voice instruction, a result of tracking the user's hand in the operative field image, or the like.

Note that, in the display in the virtual three-dimensional space 200, for an image with higher priority for the user, that is, an image that the user himself/herself wants to see, the display control section 132 may increase the refresh rate thereof or preferentially perform image processing thereon.

Furthermore, the refresh rate may be determined by whether or not the image that the user is looking at is an image with higher priority for the user. For example, in a case where the operating surgeon is looking at the operative field image, which has higher priority for him/her, the refresh rate is set to 60 Hz, and in a case where he/she is looking at the image obtained by image capture of surgical tools, which has lower priority, the refresh rate is reduced to 30 Hz. Note that which image the user is looking at is determined on the basis of a detection result of the line-of-sight of the user and the movement of the user's head (attitude of the HMD 50).

Although the divided regions into which the composite image is divided are regions corresponding the images output from the respective medical instruments (electronic instruments) in the above description, the divided regions may be partial regions of the images (divided images) output from the electronic instruments.

Figure 10:
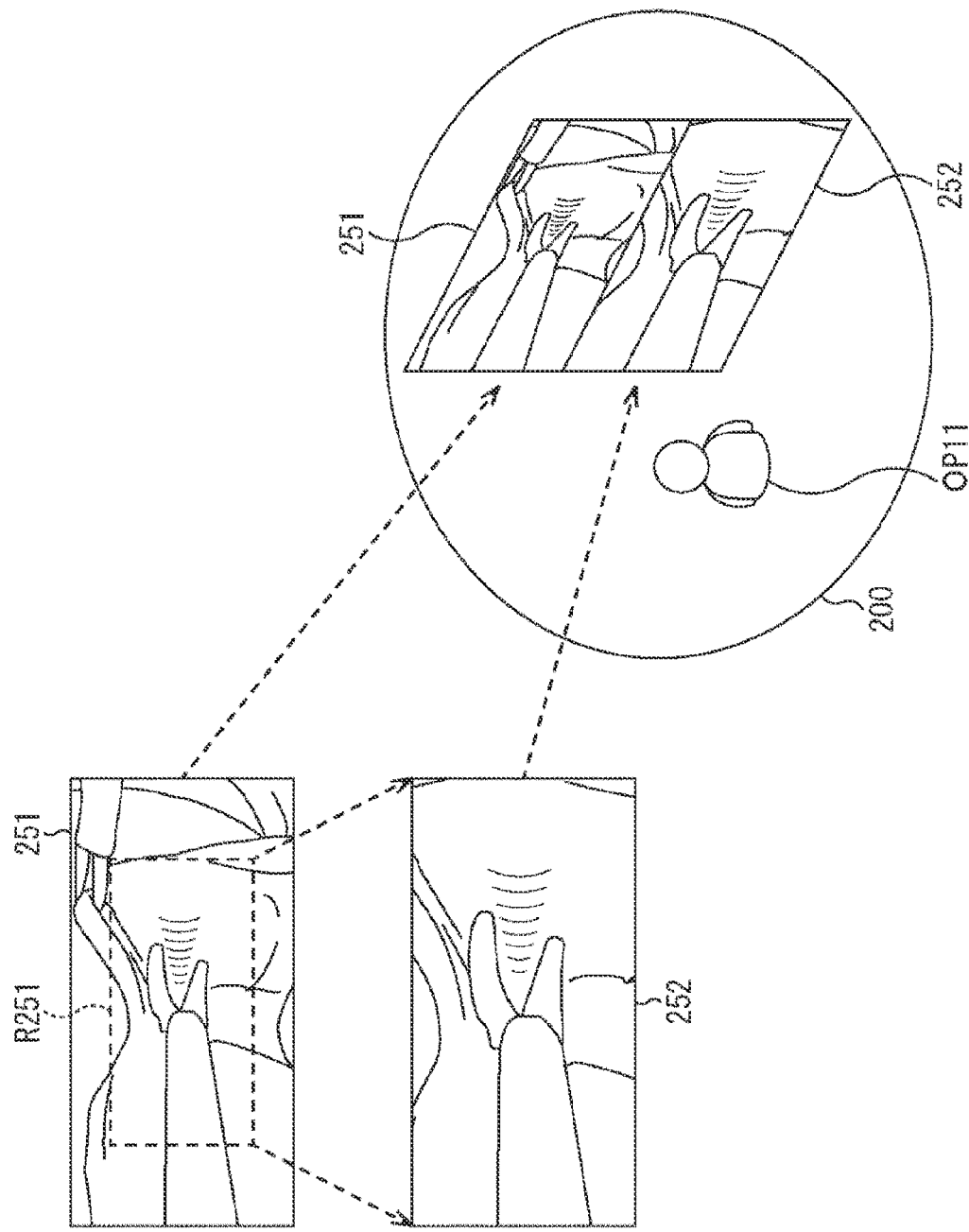
FIG. 10 is a diagram illustrating display in a virtual three-dimensional space.

For example, as shown in FIG. 10, a region including the center of the operative field image 251 and enclosed by a frame of broken lines is defined as a divided region R251. Also, an enlarged image obtained by cutting out and enlarging the divided region R251 is defined as a divided image 252, which is arranged and displayed in the virtual three-dimensional space 200 together with the original operative field image 251. The position and size of the divided region R251 in the operative field image 251 is defined by the division metadata.

In a case of using an enlarged view in an endoscopic surgical operation, it is desirable to display the enlarged image and a surrounding image at the same time in order to prevent an accident caused by a forceps or the like at a position that is no longer displayed in the enlarged view. However, in a case of displaying the enlarged image and the surrounding image on one monitor, it has been needed to decrease the display size of at least one of the enlarged image or the surrounding image. On the other hand, in a case where the enlarged image and the surrounding image are displayed on one monitor with a large display region or a plurality of monitors, the region occupied by the monitor in the operating room is increased, and cost required for installation or the like occurs.

Thus, in the example of FIG. 10, the operative field image and an enlarged image obtained by cutting out and enlarging a part thereof are arranged and displayed in the virtual three-dimensional space. Therefore, it is possible to display the enlarged image and the surrounding image at the same time without decreasing the display size and while reducing the region occupied by the monitor in the operating room and the cost required for installation or the like.

Furthermore, in order for the center of the screen to have HD resolution in displaying a 360-degrees image in the virtual three-dimensional space on the HMD, the 360-degrees image needs to have 10K resolution. In this case, transmission with a wider bandwidth and high image processing performance are required.

Concerning this, in the present embodiment, one or more regions in one image are cut out at an arbitrary position and in an arbitrary size and displayed in an arbitrary layout in the virtual three-dimensional space. Therefore, only images for needed regions in the 360-degrees image can be transmitted and displayed, and thus efficient transmission can be achieved.

Although an example where the divided images are displayed in the virtual three-dimensional space has been described above, information such as settings and parameters of the medical instrument may be included in the metadata added to the composite image, and the settings and parameters of the medical instrument may be displayed in the virtual three-dimensional space.

For example, in a case where an electric knife is used for an endoscopic surgical operation, when a voice of "output of the electric knife" spoken by the user is recognized, an output of the electric knife added to the composite image as metadata is displayed in the virtual three-dimensional space. The output of the electric knife is, for example, a frequency, a voltage, a current, a temperature, or the like.

<3. Use of line-of-sight detection result>

The HMD 50 is provided with the line-of-sight detection sensors 77L and 77R for detecting the line-of-sight of both of the left and right eyes of the wearer (user).

Thus, the display control section 132 may superimpose line-of-sight information indicating the line-of-sight position of the user on the divided image that the user is looking at on the basis of a detection result of the line-of-sight of the user using the HMD 50.

Figure 11:
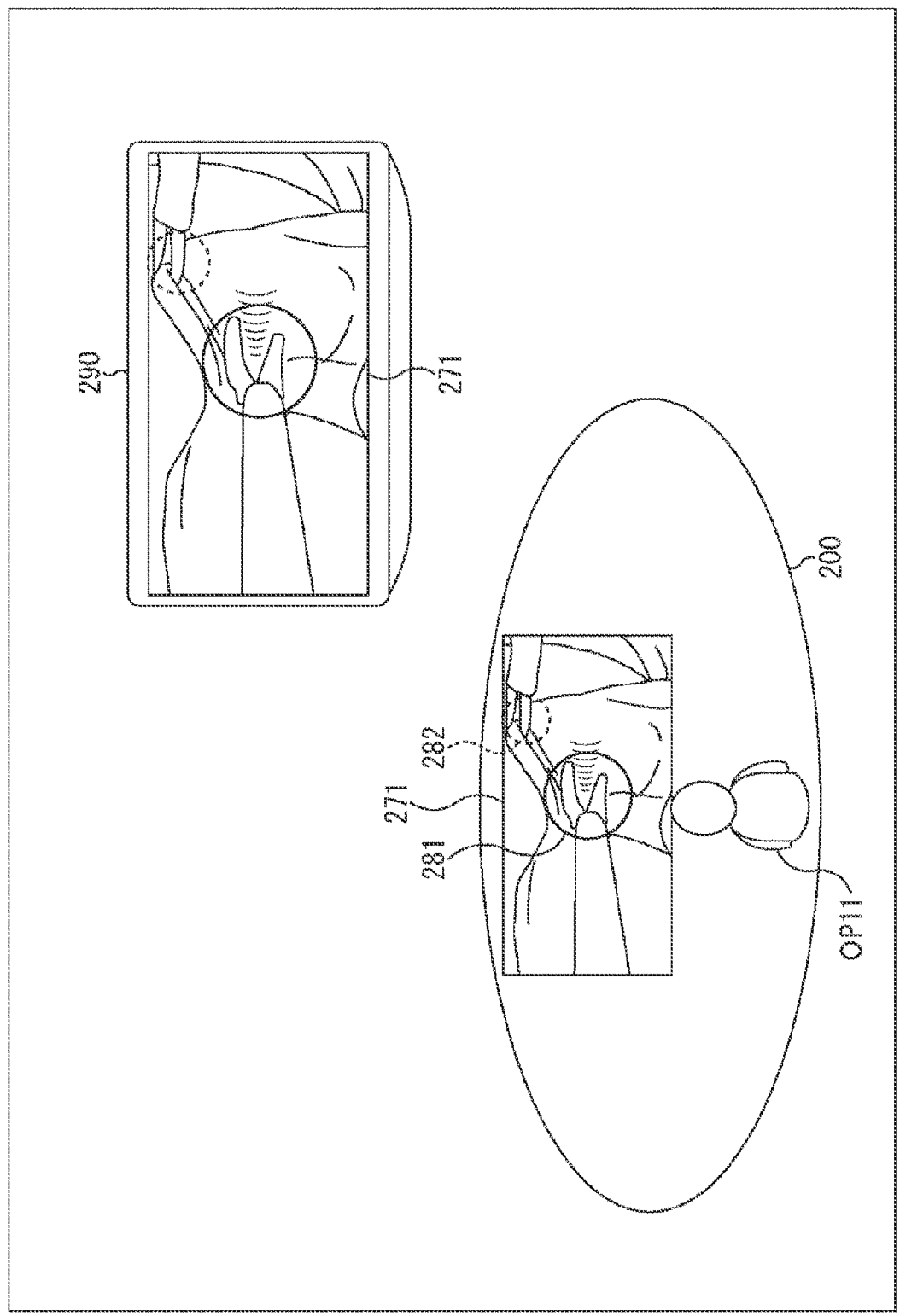
FIG. 11 is a diagram showing an example of superimposing line-of-sight information.

FIG. 11 shows an example in which line-of-sight information indicating the line-of-sight position of the user is superimposed on a divided image.

In the virtual three-dimensional space 200 shown in FIG. 11, a divided image 271, which is an operative field image, is displayed. Line-of-sight information 281 indicating the line-of-sight position of the user OP11 is superimposed at the substantial center of the divided image 271. Furthermore, line-of-sight information 282 indicating the line-of-sight position of another user (not shown) is superimposed at the upper right of the line-of-sight information 281 in the divided image 271.

Thus, in a case where the divided image 271 on which the line-of-sight information 281 of the user OP11 is superimposed is included in the divided images displayed on another HMD used by another user, and the other user is looking at the divided image, the line-of-sight information 282 of the other user is reflected in the divided image 271.

Note that line-of-sight information 281 and the line-of-sight information 282 have different colors and shapes for each corresponding user.

Furthermore, the line-of-sight information 281 and 282 of the two users are also reflected in the divided image 271 displayed on yet another HMD 50 or monitor. In the example of FIG. 11, the divided image 271 displayed in the virtual three-dimensional space 200 and on which the line-of-sight information 281 and 282 are superimposed is also displayed on a monitor 290 provided in the operating room.

In general, an HMD wearer cannot know which position in which image an HMD wearer other than himself/herself and a non-HMD wearer are looking at, and therefore it has been difficult to communicate with each other.

Concerning this, in the above-described configuration, users looking at the same image can share each other's line-of-sight position. Moreover, since the line-of-sight information can be distinguished for each user, smooth communication is enabled such as sharing the point of gaze between the operating surgeon and an assistant and designating the position of the surgical portion by the line-of-sight.

Furthermore, in a case where the point to be gazed at by one user is deviated, the one user may be urged to move the line-of-sight by outputting an alert such as by the other user's voice or flashing the line-of-sight information of the other user at the position to be gazed at.

<4. About 3D display>

In common 3D monitor viewing, a convergence angle at the time of image capture and a convergence angle at the time of viewing may be different from each other due to physical limitations such as the distance to the viewer and the screen size. The convergence angle at the time of image capture is an angle determined by the baseline length of a stereo camera and the distance to an image-capturing object, and the convergence angle at the time of viewing is an angle determined by the baseline length of both eyes of the viewer and the distance to the monitor screen.

In a case where the convergence angle is different at the time of image capture and at the time of viewing, the three-dimensional effect increases and decreases, so that the viewer has a tired feeling. In an operating room in particular, since the monitor installation position is limited, there is high possibility that the convergence angle is different at the time of image capture and at the time of viewing.

Figure 12:
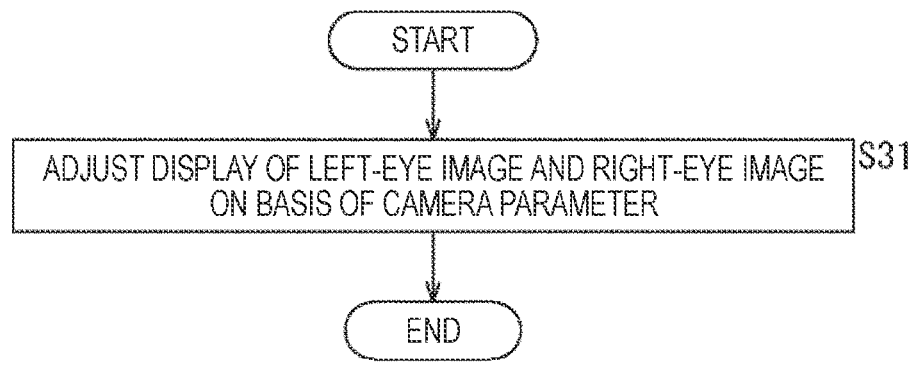
FIG. 12 is a flow chart illustrating a 3D display process.

Thus, a 3D display process for realizing display with a natural three-dimensional effect in the HMD 50 will be described with reference to the flow chart of FIG. 12.

In step S31, the display control section 132 adjusts the display of the left-eye image and the right-eye image on the basis of camera parameters.

Figure 13:
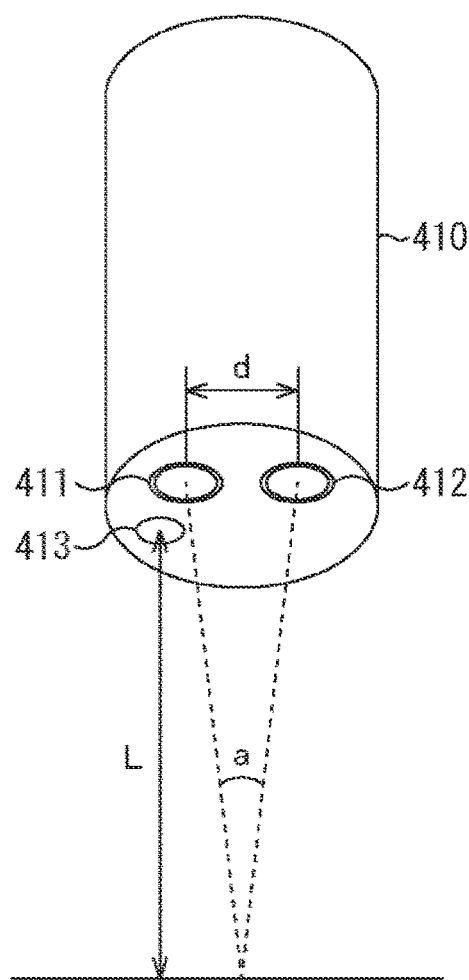
FIG. 13 is a diagram illustrating camera parameters.

FIG. 13 is diagram illustrating camera parameters. In FIG. 13, a configuration of an insertion portion 410 of the endoscope device 22 is shown.

A first camera 411 and a second camera 412 are provided at an end of the insertion portion 410. A distance measurement sensor 413 is also provided at the end of the insertion portion 410.

The first camera 411 and the second camera 412 constitute a stereo camera, and capture a right-eye image and a left-eye image that reproduce binocular parallax. The distance measurement sensor 413 measures the distance to an image-capturing object in a Time of Flight (ToF) manner, for example.

Here, as shown in FIG. 13, the baseline length, which is the distance between the respective lens optical axes of the first camera 411 and the second camera 412, is defined as d, the distance between the distance measurement sensor 413 and the image-capturing object is defined as L, and the convergence angle determined by the baseline length d and the distance L is defined as a.

In order for the right-eye image and the left-eye image captured with such camera parameters to be displayed on the HMD 50 with a natural three-dimensional effect, the convergence angle at the time of viewing is set to be the same as the convergence angle a at the time of image capture.

Figure 14:
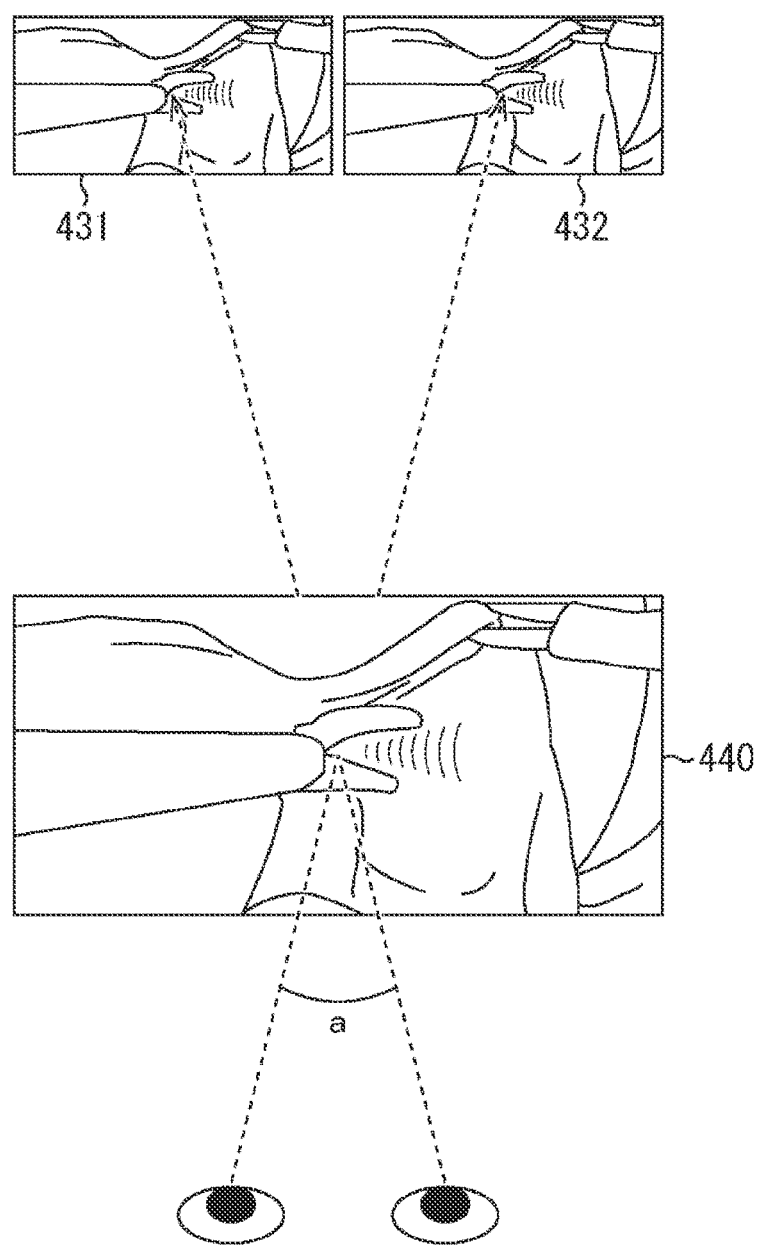
FIG. 14 is a diagram illustrating adjustment of display of a right-eye image and a left-eye image.

Specifically, the display layout of the right-eye image 431 and the left-eye image 432 shown in FIG. 14 is adjusted such that the convergence angle at time of viewing becomes the convergence angle a on the basis of the baseline length d, the distance L, and the baseline length of both eyes of the viewer. Specifically, the display size, angle, display position of the right-eye image 431 and the left-eye image 432 in the display sections 75R and 75L of the HMD 50 are adjusted.

At this time, the display metadata (arrangement information and display size information) may be changed on the basis of the camera parameters, and the display size, angle, display position of the right-eye image 431 and the left-eye image 432 may be adjusted.

Therefore, a 3D image 440 displayed in the virtual three-dimensional space is displayed with a natural three-dimensional effect, and the tired feeling given to the viewer can be reduced.

<5. Application example>

An example where the surgery support system according to the present embodiment is applied to an endoscopic surgical system has been described above. There is no limitation thereto, and the surgery support system according to the present embodiment can also be applied to a microscopic surgery system using a surgical video microscope device as an observation medical instrument for observing the inside of the patient's body. In this case, a video microscope device instead of the endoscope device 22 is provided in the surgery support system 10 in FIG. 1.

Furthermore, although an image displayed in the virtual three-dimensional space is a real-time moving image in the above description, a moving image that is recorded in advance may also be included. For example, by displaying a moving image obtained by recording in advance the procedures, techniques, and the like of the surgical operation in the virtual three-dimensional space as an educational content, a vicarious experience of the surgical operation can be provided without attendance at the actual surgical operation.

Moreover, the technique according to the present embodiment may be applied to a system other than the surgery support system. For example, by connecting HMDs to each other via a network, a system can be provided in which users have a communication such as a chat or play a bidirectional game while viewing various images.

Note that the display in the virtual three-dimensional space described above may also be realized in a ceiling-hung monitor, without limitation to the HMD 50.

<6. Hardware configuration>

Next, an example hardware configuration of the operating room server as an information processing device constituting the surgery support system according to the present embodiment will be described in detail with reference to FIG. 15.

Figure 15:
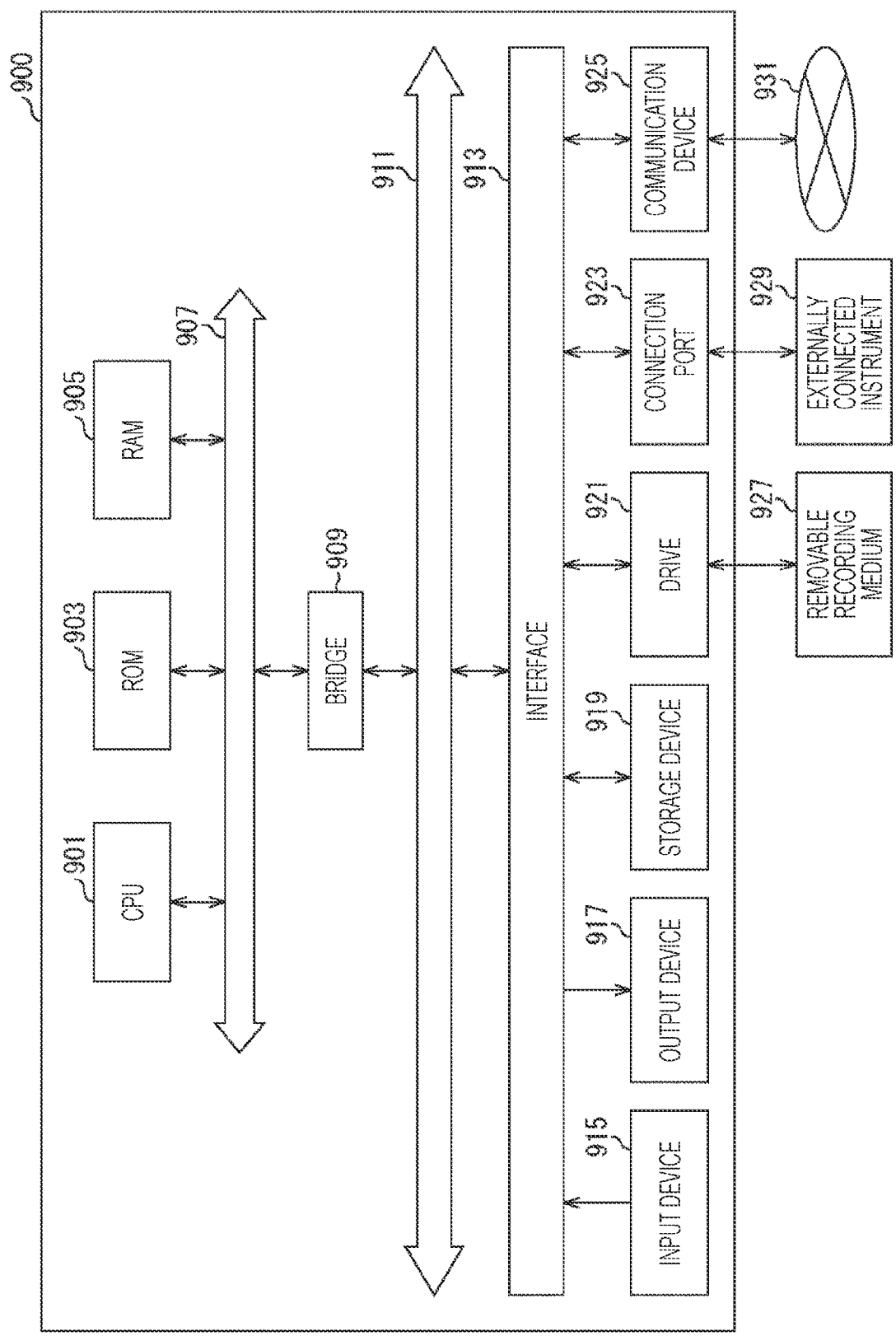
FIG. 15 is a block diagram showing an example hardware configuration of an information processing device.

FIG. 15 is a block diagram showing an example hardware configuration of an information processing device 900 constituting the surgery support system according to the present embodiment.

As shown in FIG. 15, the information processing device 900 includes a CPU 901, a ROM 903, and a RAM 905. Moreover, the information processing device 900 includes a host bus 907, a bridge 909, an external bus 911, an interface 913, an input device 915, an output device 917, and a storage device 919. Note that the information processing device 900 may include a drive 921, a connection port 923, and a communication device 925.

The CPU 901 functions as an arithmetic processing device and a control device, and controls all or part of the operations in the information processing device 900 according to various programs recorded on the ROM 903, the RAM 905, the storage device 919, or a removable recording medium 927.

The ROM 903 stores programs, arithmetic parameters, and the like used by the CPU 901. The RAM 905 primarily stores programs used by the CPU 901, parameters changing at any time during execution of the programs, and the like. These are connected to each other by the host bus 907 constituted by an internal bus such as a CPU bus. Note that each component of the operating room server 30 described with reference to FIG. 3 is realized by the CPU 901, for example.

The host bus 907 is connected to the external bus 911 such as a Peripheral Component Interconnect/Interface (PCI) bus via the bridge 909. The input device 915, the output device 917, the storage device 919, the drive 921, the connection port 923, and the communication device 925 are connected to the external bus 911 via the interface 913.

The input device 915 is, for example, an operation means operated by the user, such as a mouse, a keyboard, a touch panel, a button, a switch, a lever, and a pedal, or a microphone capable of voice input. Furthermore, the input device 915 may be, for example, a remote control means (a so-called remote controller) using infrared light or other radio waves, or may be an externally connected instrument 929 such as a mobile phone or a PDA that supports the operation of the information processing device 900.

The input device 915 includes, for example, an input control circuit that generates an input signal on the basis of information input by the user using the above-described operation means and outputs it to the CPU 901, and the like. The user can input various data to and provide instructions of processing operations to the information processing device 900 by operating the input device 915.

The output device 917 includes a device capable of visually or audibly notifying the user of acquired information. Specifically, the output device 917 is constituted as a display device such as a CRT display device, a liquid crystal display device, a plasma display device, an EL display device, and a lamp, an audio output device such as a speaker and headphones, or a printer device, or the like.

The output device 917 outputs results obtained by various processes performed by the information processing device 900, for example. Specifically, the display device displays results obtained by various processes performed by the information processing device 900 in texts or images. On the other hand, the audio output device converts an audio signal including reproduced audio data, acoustic data, and the like into an analog signal and outputs it.

The storage device 919 is a data storage device constituted as an example of a storage section of the information processing device 900. The storage device 919 is constituted by, for example, a magnetic storage section device such as a hard disk drive (HDD), a semiconductor storage device, an optical storage device, an optical magnetic storage device, or the like. The storage device 919 stores programs executed by the CPU 901, various data, and the like.

The drive 921 is a reader/writer for recording media, and is built in or externally attached to the information processing device 900. The drive 921 reads information recorded on the mounted removable recording medium 927 such as a magnetic disk, an optical disk, a magneto-optical disk, or a semiconductor memory, and outputs it to the RAM 905. Furthermore, the drive 921 can also write records in the mounted removable recording medium 927 such as a magnetic disk, an optical disk, a magneto-optical disk, or a semiconductor memory.

The removable recording medium 927 is, for example, a DVD medium, a HD-DVD medium, a Blu-ray (registered trademark) medium, or the like. Furthermore, the removable recording medium 927 may be CompactFlash (registered trademark) (CF), a flash memory, a secure digital (SD) memory card, or the like. Moreover, the removable recording medium 927 may be, for example, an integrated circuit (IC) card equipped with a non-contact IC chip, an electronic instrument, or the like.

The connection port 923 is a port for directly connecting the externally connected instrument 929 to the information processing device 900. Examples of the connection port 923 include a Universal Serial Bus (USB) port, an IEEE 1394 port, a Small Computer System Interface (SCSI) port, and an SDI port. Other examples of the connection port 923 include a RS-232C port, an optical audio terminal, a High-Definition Multimedia Interface (HDMI) (registered trademark) port, and the like. By connecting the externally connected instrument 929 to the connection port 923, the information processing device 900 acquires various data directly from the externally connected instrument 929 and provides various data to the externally connected instrument 929.

The communication device 925 is, for example, a communication interface including a communication device for connecting to a communication network (network) 931 or the like. The communication device 925 is, for example, a communication card for wired or wireless local area network (LAN), Bluetooth (registered trademark), or wireless USB (WUSB). Furthermore, the communication device 925 may be a router for optical communication, a router for Asymmetric Digital Subscriber Line (ADSL), a modem for various communications, or the like.

For example, the communication device 925 can send/receive signals to/from the Internet and other communication instruments according to a predetermined protocol such as TCP/IP, for example. Furthermore, the communication network 931 connected to the communication device 925 may constituted by a network connected in a wired or wireless manner, or the like. The communication network 931 may be, for example, the Internet or a home LAN, or may be a communication network on which infrared communication, radio wave communication, or satellite communication is performed.

Each component of the information processing device 900 described above may be constituted by using a general-purpose member, or may be constituted by hardware dedicated to the function of each component. Therefore, it is possible to appropriately change the hardware configuration used according to the technical level at each time when the present embodiment is implemented.

Moreover, it is possible to create a computer program for realizing each function of the information processing device 900 constituting the surgery support system according to the present embodiment and implement it on a personal computer or the like. Furthermore, it is also possible to provide a computer-readable recording medium in which such a computer program is stored. The recording medium is, for example, a magnetic disk, an optical disk, a magneto-optical disk, a flash memory, or the like. Furthermore, the computer program may be distributed via a network, for example, without using a recording medium.

Note that the display control device constituting the surgery support system according to the present embodiment can also be constituted in a manner similar to the information processing device 900 of FIG. 15.

Furthermore, in the surgery support system according to the present embodiment, the information processing device (operating room server 30) and the display control device (display control device 40) can be constituted as one device.

Embodiments of the present disclosure are not limited to the embodiments described above, and various modifications are possible without departing from the spirit of the present disclosure.

For example, the present disclosure can take a configuration of cloud computing in which one function is distributively and jointly processed by a plurality of devices via a network.

Furthermore, each step described in the flow charts described above can be performed not only by one device but also distributively performed by a plurality of devices.

Moreover, in a case where one step includes a plurality of processes, the plurality of processes included in the one step can be performed not only by one device but also distributively performed by a plurality of devices.

Furthermore, the present disclosure can also have the following configurations.

(1)

A surgery support system including:

an information processing device including:

a composition section that generates a composite image by compositing images output from a plurality of electronic instruments including a medical instrument; and a metadata addition section that adds, to the composite image, first metadata related to division of the composite image; and a display control device including:

a display control section that controls a display device to display, in a virtual three-dimensional space, divided images obtained by dividing the composite image into a plurality of divided regions on the basis of the first metadata.

(2)

The surgery support system according to (1), in which the first metadata includes information indicating each of the divided regions.

(3)

The surgery support system according to (2), in which the divided regions are regions corresponding to the images output from the electronic instruments.

(4)

The surgery support system according to (2), in which the divided regions include a partial region of the images output from the electronic instruments, the display control section controls display of an enlarged image in which the partial region of the images is enlarged, as the divided images.

(5)

The surgery support system according to any one of (1) to (4), in which the metadata addition section adds, to the composite image, second metadata related to display of each of the divided images in the virtual three-dimensional space, and the display control section controls display of the divided images in the virtual three-dimensional space on the basis of the second metadata.

(6) The surgery support system according to (5), in which the second metadata includes information indicating arrangement of each of the divided images in the virtual three-dimensional space.

(7) The surgery support system according to (5) or (6), in which the second metadata includes information indicating a display size of each of the divided images in the virtual three-dimensional space.

(8) The surgery support system according to any one of (5) to (7), in which the composition section generates the composite image by compositing the images output from the plurality of electronic instruments in a combination corresponding to a template selected by a user using the display device.

(9) The surgery support system according to (8), in which the metadata addition section adds, to the composite image, the first and second metadata that realize a display manner of the divided images corresponding to the template.

(10) The surgery support system according to (8) or (9), in which the template is prepared for each type of the user.

(11) The surgery support system according to any one of (5) to (10), in which the metadata addition section changes a content of the first and second metadata on the basis of an instruction from a user using the display device.

(12) The surgery support system according to any one of (1) to (11), in which the composition section adds time information to each of the images output from the plurality of electronic instruments in compositing the images.

(13) The surgery support system according to any one of (1) to (12), in which the display control section superimposes line-of-sight information indicating a line-of-sight position of a user using the display device on the divided images on the basis of a detection result of a line-of-sight of the user.

(14) The surgery support system according to (13), in which in a case where the divided images on which the line-of-sight information is superimposed are included in the divided images displayed on another display device used by another user, the display control section causes other line-of-sight information indicating a line-of-sight position of the other user to be reflected in the divided images.

(15) The surgery support system according to any one of (1) to (14), in which the display device includes an HMD.

(16) The surgery support system according to any one of (1) to (14), in which the display device includes a ceiling-hung monitor.

(17) The surgery support system according to any one of (1) to (16), in which the medical instrument includes an endoscope device.

(18) The surgery support system according to any one of (1) to (16), in which the medical instrument includes a video microscope device.

(19) A display control device including: a display control section that controls a display device to display, in a virtual three-dimensional space, divided images obtained by dividing a composite image into a plurality of divided regions on the basis of metadata related to division of the composite image, the composite image generated by compositing images output from a plurality of electronic instruments including a medical instrument.

(20) A display control method including: controlling, by a display control device, a display device to display, in a virtual three-dimensional space, divided images obtained by dividing a composite image into a plurality of divided regions on the basis of metadata related to division of the composite image, the composite image generated by compositing images output from a plurality of electronic instruments including a medical instrument.

REFERENCE SIGNS LIST

10 Surgery support system
21 Operating room camera
22 Endoscope device
23 Medical instrument
30 Operating room server
40, 40-1 to 40-3 Display control device
50, 50-1, 50-2 HMD
60 Monitor
111 Composition section
112 Metadata addition section
113 I/F section
121 Time information addition section
131 I/F section
132 Display control section

The invention claimed is:
1. A surgery support system, comprising:
a first display device; and
an information processing device including circuitry configured to:
composite a plurality of images outputted from a plurality of electronic instruments, wherein the plurality of electronic instruments includes a medical instrument;
generate a composite image based on the composition of the plurality of images;
add first metadata to the generated composite image, wherein
the first metadata includes information that indicates a type of each electronic instrument of the plurality of electronic instruments from which the plurality of images is outputted;
divide the generated composite image into a plurality of regions based on the addition of the first metadata to the generated composite image;
add, to the composite image, second metadata related to display of each of the plurality of regions in a virtual three-dimensional space; and control the first display device to display, in the virtual three-dimensional space, the plurality of regions based on the second metadata.

2. The surgery support system according to claim 1, wherein
the first metadata includes information indicating each of the plurality of regions.

3. The surgery support system according to claim 2, wherein
the plurality of regions corresponds to the plurality of images output from the plurality of electronic instruments.

4. The surgery support system according to claim 2, wherein
the plurality of regions includes a partial region of the plurality of images output from the plurality of electronic instruments,
the circuitry is further configured to control the first display device to display an enlarged image in which the partial region of the plurality of images is enlarged as divided images.

5. The surgery support system according to claim 1, wherein
the second metadata includes information indicating arrangement of each of the plurality of regions in the virtual three-dimensional space.

6. The surgery support system according to claim 1, wherein
the second metadata includes information indicating a display size of each of the plurality of regions in the virtual three-dimensional space.

7. The surgery support system according to claim 1, wherein
the circuitry is further configured to generate the composite image based on a template selected by a user of the first display device.

8. The surgery support system according to claim 7, wherein
the circuitry is further configured to add, to the composite image, the first metadata and the second metadata that realize a display manner of the plurality of regions corresponding to the template.

9. The surgery support system according to claim 7, wherein the template is associated with each type of the user.

10. The surgery support system according to claim 1, wherein
the circuitry is further configured to change a content of the first metadata and the second metadata based on an instruction from a user of the first display device.

11. The surgery support system according to claim 1, wherein
the circuitry is further configured to add time information to each of the plurality of images output from the plurality of electronic instruments in the composition of the plurality of images.

12. The surgery support system according to claim 1, wherein
the circuitry is further configured to superimpose first line-of-sight information indicating a line-of-sight position of a first user on the plurality of regions based on a detection result of a line-of-sight of the first user.

13. The surgery support system according to claim 12, wherein
in a case where the plurality of regions on which the first line-of-sight information is superimposed are included in the plurality of regions displayed on a second display device used by a second user, the circuitry is further configured to cause second line-of-sight information indicating a line-of-sight position of the second user to be reflected in the plurality of regions.

14. The surgery support system according to claim 1, wherein the first display device includes a head mounted display (HMD).

15. The surgery support system according to claim 1, wherein the first display device includes a ceiling-hung monitor.

16. The surgery support system according to claim 1, wherein
the medical instrument includes one of an endoscope device or a video microscope device.

17. A display control device, comprising:
circuitry configured to control a display device to display, in a virtual three-dimensional space, a plurality of regions of a composite image, wherein
the plurality of regions of the composite image is based on first metadata,
the first metadata includes information that indicates a type of each electronic instrument of a plurality of electronic instruments from which a plurality of images is outputted,
the display of the plurality of regions in the virtual three-dimensional space is based on second metadata added to the composite image,
the second metadata is related to the display of each of the plurality of regions, and
the composite image is generated by compositing the plurality of images output from the plurality of electronic instruments including a medical instrument.

18. A display control method, comprising:
controlling a display device to display, in a virtual three-dimensional space, a plurality of regions of a composite image, wherein
the plurality of regions of the composite image is based on first metadata,
the first metadata includes information that indicates a type of each electronic instrument of a plurality of electronic instruments from which a plurality of images is outputted,
the display of the plurality of regions in the virtual three-dimensional space is based on second metadata added to the composite image,
the second metadata is related to the display of each of the plurality of regions, and
the composite image generated by compositing the plurality of images output from the plurality of electronic instruments including a medical instrument.

19. The surgery support system according to claim 14, wherein the circuitry is further configured to control the first display device to re-arrange the plurality of regions with respect to a point of view of a user of the first display device based on a movement of a head of the user.

* * * * *